US006010475A

United States Patent [19]
Thomas et al.

[11] Patent Number: 6,010,475
[45] Date of Patent: Jan. 4, 2000

[54] APPARATUS FOR THE TREATMENT OF BLOOD BY EXTRACORPOREAL CIRCULATION AND PROCESS OF MANUFACTURE

[75] Inventors: Michel Thomas, Serezin Du Rhone; Pierre Valette, Lyons, both of France

[73] Assignee: Hospal Industrie, Meyzieu, France

[21] Appl. No.: 08/933,032

[22] Filed: Sep. 18, 1997

[30] Foreign Application Priority Data

Sep. 19, 1996 [FR] France ................................. 96 11631
Nov. 8, 1996 [FR] France ................................. 96 13997

[51] Int. Cl.⁷ ........................... A61M 37/00; A61M 1/14; A61L 13/00
[52] U.S. Cl. ................................. 604/4; 422/44; 422/48; 427/2.25
[58] Field of Search ........................... 422/48, 44; 604/4; 427/2.25

[56] References Cited

U.S. PATENT DOCUMENTS

| | | |
|---|---|---|
| 5,004,548 | 4/1991 | Richalley et al. . |
| 5,098,960 | 3/1992 | Frautschi et al. .................... 525/359.3 |
| 5,098,977 | 3/1992 | Frautschi et al. ....................... 527/313 |
| 5,128,170 | 7/1992 | Matsuda et al. ............................. 427/2 |
| 5,162,102 | 11/1992 | Nogawa et al. . |
| 5,229,172 | 7/1993 | Cahalan et al. . |
| 5,240,994 | 8/1993 | Brink et al. . |
| 5,250,613 | 10/1993 | Bergstrom et al. ..................... 525/54.1 |
| 5,532,311 | 7/1996 | Sirvio et al. ............................ 525/54.2 |
| 5,643,681 | 7/1997 | Voorhees et al. ....................... 428/483 |
| 5,645,931 | 7/1997 | Fan et al. ................................. 428/334 |
| 5,702,818 | 12/1997 | Cahalan et al. ......................... 428/409 |
| 5,702,823 | 12/1997 | Forrestal et al. ....................... 458/450 |
| 5,738,902 | 4/1998 | Forrestal et al. ....................... 427/2.12 |
| 5,811,151 | 9/1998 | Hendriks et al. ....................... 427/2.24 |
| 5,863,501 | 1/1999 | Cosentino ................................. 422/48 |

FOREIGN PATENT DOCUMENTS

| | | |
|---|---|---|
| 0 704 223 A1 | 4/1993 | European Pat. Off. . |
| WO89/09246 | 10/1989 | WIPO . |
| WO97/14448 | 4/1997 | WIPO . |
| WO9832474 | 7/1998 | WIPO . |

OTHER PUBLICATIONS

D. Pegues et al., "Anaphylactoid Reactions Associated With Reuse of Hollow–Fiber Hemodialyzers and ACE Inhibitors", Kidney International, 42:1232–1237 (1992).

*Primary Examiner*—Corrine McDermott
*Assistant Examiner*—Cheryl L. Huseman
*Attorney, Agent, or Firm*—Finnegan, Henderson, Farabow, Garrett & Dunner, L.L.P.

[57] ABSTRACT

An apparatus for the treatment of blood or plasma by extracorporeal circulation includes a compartment for the circulation of blood. The compartment is provided with two accesses and has at least one inner surface intended to be coated, after sterilization, with at least one molecular layer of a substance soluble in an aqueous solution. The aqueous solution is capable of increasing the bicompatibility of the inner surface of the compartment. A determined quantity of the substance is deposited inside the blood compartment, at one of the accesses, in a form such that the substance is capable of undergoing, substantially without deterioration, an irradiation capable of sterilizing the apparatus. The quantity of substance is determined such that the circulation of a determined volume of aqueous solution through the blood compartment, starting from the access where the substance has been deposited, should result in the formation, by durable bonding, of at least one molecular layer of the substance on the inner surface of the blood compartment to be treated.

20 Claims, 9 Drawing Sheets

APPARATUS FOR THE TREATMENT OF BLOOD BY EXTRACORPOREAL CIRCULATION AND PROCESS OF MANUFACTURE

BACKGROUND OF THE INVENTION

1. Field of the Invention

The present invention relates to an apparatus for the treatment of blood by extracorporeal circulation and to a process of manufacture of this apparatus.

2. Description of the Related Art

Apparatuses for the treatment of blood by extracorporeal circulation are employed in various medical or paramedical applications such as: treatment of renal insufficiency by dialysis or haemofiltration, plasmapheresis and aphaeresis with therapeutic and nontherapeutic aim, blood oxygenation, immunopurification, and the like.

A common feature of all these apparatuses is that they comprise a blood compartment provided with two accesses, in which, during the treatment in question the patient's blood is circulated. To do this, a blood withdrawal line is connected between a blood vessel of the patient and an access, employed as entry, of the blood compartment; a blood return line is connected between the other access of the blood compartment, employed as exit, and a blood vessel of the patient; and the patient's blood is circulated in this extracorporeal circuit looped onto the patient, by means of a pump, usually placed in the withdrawal line.

The blood compartment of these apparatuses is generally bounded by a portion of the walls of a casing of the apparatus and by a wall of an active member of the apparatus, by means of which the treatment of blood is performed. By way of example, in a dialyser containing hollow fibres, the blood compartment is bounded by the interior of the fibres of a bundle of hollow fibres, constituting a semipermeable membrane, by the external surface of the discs of adhesive employed for attaching the bundle of fibres to the two ends of a tubular casing of the apparatus, and by two end fittings secured to each end of the casing.

All the materials employed in the manufacture of these apparatuses are chosen to be as biocompatible as possible, so that the reactions (coagulation in particular) which take place when the blood comes into contact with a foreign material do not take place or take place at relatively benign levels.

It is known to treat, in bulk or at the surface, the materials intended to be in contact with blood in order to improve their biocompatibility. The known treatments take place either during the manufacture of some part or other of an apparatus (bulk treatment), or after the various parts of the apparatus have been assembled and before sterilization of the apparatus, or, extemporaneously, just before the apparatus is employed.

A problem which is particularly tough to solve arises when attempts are made to improve the biocompatibility of the active member of an apparatus (for example a dialysis membrane) while conforming to the following conditions:

1) the choice of the substance employed for the treatment and the treatment methods must result in the modification of a known active member, this modification having the effect of improving the biocompatibility of the active member while preserving all the known qualities (for example, in the case of a dialysis/haemofiltration membrane: diffusive and convective transfer performance, adsorption capacity for undesirable substances, and the like);

2) sterilization of the apparatus must not affect the treatment;

3) the treatment must not require any special handling by the user.

SUMMARY OF THE INVENTION

The objective of the invention is to propose a process for the manufacture of an apparatus which satisfies these conditions.

More specifically, the objective of the invention is to propose a process of manufacture of an apparatus satisfying the conditions specified above and in which the active member, before treatment, has negative charges at the surface. When blood comes into contact with a negatively charged surface, it is the site of a biological phenomenon called activation of the contact phase, which manifests itself in the generation of active substances, kallikrein and factor XIIa, from inactive substances, prekallikrein and factor XII.

The activation of the contact phase is benign in itself, but when it takes place simultaneously with some perturbing factors (taking of hypotensive medications of IEC type by the patient, dilution of the blood entering the apparatus filled with saline solution, accompanying lowering of the pH) it seems to be the source of undesirable so-called anaphylactoid reactions which manifest themselves a few minutes after the beginning of the treatment as various symptoms, including an overall feeling of hotness, numbness of the fingers, the lips or the tongue, panting, nausea and laryngeal oedema. It should be remembered that anaphylactoid reactions are not exclusively linked with the use of medical apparatuses in which the blood compartment has a negatively charged inner surface. These reactions have been noted with exchangers which have membranes of different chemical compositions, sometimes when first employed, sometimes after several utilizations when the exchangers, instead of being discarded after a single use, are used again many times and are recycled after each use. An example of an exchanger in which a first use has been accompanied by an undesirable reaction is a dialyser which has a polymethyl methacrylate and polyacrylonitrile membrane. Reactions associated with the reuse of dialysers with a cellulose acetate and polysulphone membrane have been just as well documented (see "Anaphylactoid reactions associated with reuse of hollow-fiber hemodialyzers and ACE inhibitors" in Kidney International, vol. 42 (1992), pp. 1232–1237).

There is provided, in accordance with one aspect of the invention, a process for improving the biocompatibility of an apparatus for the treatment of blood or plasma by extracorporeal circulation. The apparatus has a compartment for the circulation of blood provided with two accesses. In the process, a determined quantity of a substance is deposited in the blood compartment at at least one of the accesses. The substance is deposited in a form such that the substance is capable of undergoing, substantially without deterioration, an irradiation capable of sterilizing the apparatus.

The substance is capable of dissolving in an aqueous solution and of being durably bonded to an inner surface of the blood compartment in order to increase the bicompatibility of the apparatus. The quantity of substance is determined such that the circulation of a determined volume of aqueous solution through the blood compartment, starting from the access where the substance has been deposited, should result in the formation of at least one molecular layer of the substance, by durable bonding, to the inner surface of the blood compartment.

The process also includes sterilizing the apparatus and, before the utilization of the apparatus, circulating a determined volume of aqueous solution through the blood compartment. The circulation of aqueous solution starts from the access where the substance has been deposited, so as to carry the substance into contact with the inner surface of the blood compartment and to cause the formation of at least one durable molecular layer of the substance on the inner surface of the blood compartment.

Within the meaning of the invention, the ability to dissolve in an aqueous solution, which is a characteristic of the substance, must be understood as a function of the objective to be met. That is at the outcome of the process, at least one molecular layer of the substance is bonded to the inner surface to be treated of the blood compartment. In addition, when it would be undesirable that the substance should be introduced into the patient's blood, it is necessary that at the outcome of the process all the substance should have been dissolved and that no residue should remain in the blood compartment. In other words, this ability comprises both the physical ability to dissolve in an aqueous solution and a speed of dissolution, which depends on a number of parameters: volume of aqueous solution employed, temperature of the aqueous solution, and flow rate of the aqueous solution in the blood compartment. If these parameters are fixed, for example by deciding that the last stage of the process will be carried out immediately before the use of the apparatus during the procedure for starting up ("priming") the apparatus, then the substance must be chosen, among other criteria, so that the objective of the invention can be met by circulating through the blood compartment, for example, two liters of physiological saline at ambient temperature (20° C. to 24° C.) at a flow rate of 200 ml/min (conventional conditions for starting up a dialyser in a dialysis centre).

The process has two major advantages: on the one hand, the surface modified by the substance is obtained only after sterilization of the apparatus, with the result that this modified, biocompatible surface does not run the risk of being damaged by a highly energetic sterilization like sterilization using $\gamma$ irradiation; on the other hand, when the aqueous solution employed is the solution for starting up the exchanger, the utilization of the apparatus by the user is exactly identical with that of any apparatus of the same type.

According to an alternative form of the invention, in an apparatus in which the blood compartment has two symmetrical accesses, the determined quantity of substance is deposited at each access so that, whatever the direction of subsequent circulation of the aqueous solution through the blood compartment, a molecular layer of the substance is formed on the inner surface to be treated.

Another subject of the invention is a process of manufacture of an apparatus for the treatment of blood or plasma by extracorporeal circulation. The apparatus has a compartment for the circulation of blood provided with two accesses. The process includes, before a stage of sterilization of the apparatus, the step of depositing in the blood compartment, at at least one of the accesses, a determined quantity of a substance in a form such that the substance is capable of undergoing, substantially without deterioration, an irradiation capable of sterilizing the apparatus.

The substance is capable of dissolving in an aqueous solution and of durably bonding to an inner surface of the blood compartment in order to increase the biocompatibility of the apparatus. The quantity of substance is determined such that the circulation of a determined volume of aqueous solution through the blood compartment, starting from the access where the substance has been deposited, should result in the formation, by durable bonding, of at least one molecular layer of the substance on the inner surface of the blood compartment.

This process has the advantage of being very easy to apply industrially.

Another subject of the invention, is an apparatus for the treatment of blood or of plasma resulting from the use of the process of manufacture described above.

According to an alternative form of the invention, the surface to be treated has negative charges and the substance is cationic, with the result that a molecular layer of the surface masks the negative charges of the surface.

In one embodiment of the invention the apparatus is a haemodialyser/haemofilter provided with a membrane manufactured from a copolymer of acrylonitrile and of sodium methallylsulphonate (membrane known under the trade name AN69). The substance chosen for improving the biocompatibility of this membrane is polyethyleneimine (PEI) which has a molecular mass (measured by light scattering) of between approximately 10 and approximately 2000 k dalton. The quantity of PEI (molecular mass 25 k dalton) deposited at one or each blood access is preferably between approximately 5 and 10 mg per $m^2$ of membrane intended to be in contact with the blood.

This apparatus does not activate the contact phase and has the same performance as an unmodified haemodialyser/haemofilter.

BRIEF DESCRIPTION OF THE DRAWINGS

Other characteristics and advantages of the invention will appear on reading the description which follows. Reference will be made to the attached drawings in which.

DESCRIPTION OF THE PREFERRED EMBODIMENTS

To illustrate the invention, a particular type of apparatus for the extracorporeal treatment of blood will be described, which is employed for alleviating renal insufficiency.

Figure 1:
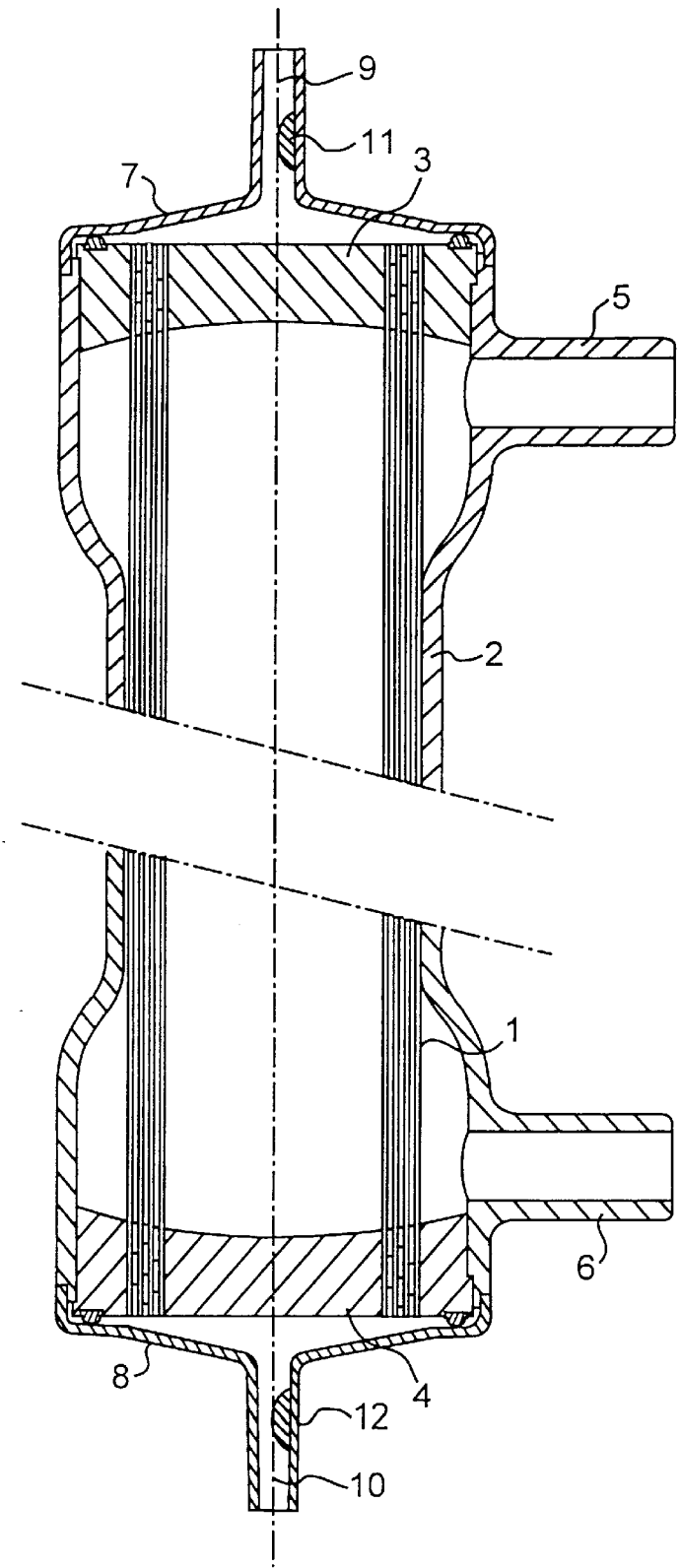
FIG. 1 shows a diagrammatic view in lengthwise section of a dialyser with hollow fibres according to the invention.

A haemodialyser/haemofilter conventionally includes two compartments separated by a semipermeable membrane. A first compartment is intended to be connected by means of a withdrawal line and a return line to the patient's vascular circuit, whereas the second compartment has an entry optionally connected to a source of dialysis liquid (treatment by haemodialysis and haemodiafiltration) and an exit connected to a discharge for spent liquid (spent dialysate and/or ultrafiltrate). The membrane is chosen so as to permit the diffusive and/or convective transfers of the metabolic wastes from the blood compartment towards the compartment for spent liquid. The membrane may be manufactured in the form of a planar membrane or of a bundle of hollow fibres. A dialyser with a planar membrane includes a strip of planar membrane folded accordion-style, an insert plate being introduced into all the folds opening on the same side. As can be seen in FIG. 1, a dialyser with hollow fibres includes a bundle of hollow fibres 1, which is placed in a tubular casing 2. The bundle of hollow fibres 1 is held at its two ends by a disc of adhesive 3, 4. In addition to bonding the fibres together, the purpose of the discs of adhesive 3, 4 is to delimit in the tubular casing 2 a leaktight compartment to which access is given by two small tubes 5, 6, perpendicular to the axis of the casing 2. At each end of the casing 2 is attached an end fitting 7, 8 including a small axial access tube 9, 10. The two small tubes 9, 10 are symmetrical. The blood compartment of this apparatus consists of the internal space delimited between each disc of adhesive 3, 4 and the end fitting 8, 9 closing the corresponding end of the tubular casing 2, and by the interior of the hollow fibres.

In accordance with the invention, to improve the biocompatibility of this apparatus by modifying an inner surface of the blood compartment, a determined quantity of a substance soluble in an aqueous solution and capable of modifying the surface involved in the desired manner is deposited in each end fitting 8, 9 after the apparatus has been assembled as shown in FIG. 1. The quantity of substance is chosen such that, after circulation of a determined quantity of aqueous solution through the blood compartment, at least one molecular layer of the substance covers the surface whose biocompatibility is to be improved. The quantity of substance is deposited in the form of a drop 11, 12 by means of a conventional injection device. The drop is formed either by a gel of the substance or by a matrix material in which the substance is incorporated.

After deposition of the substance has been performed, the small access tubes 5, 6, 9, 10 are stoppered and the apparatus can be sterilized, for example by means of ethylene oxide or by γ irradiation.

The use of any apparatus for the treatment of blood or plasma by extracorporeal circulation includes a preliminary starting-up stage during which the blood compartment is rinsed and filled with a sterile aqueous solution.

In accordance with the invention, this stage of preparation of the apparatus is exploited for dissolving the treatment substance and bringing it into contact with the surface to be treated. Before the beginning of the actual dialysis session, the user connects one of the small access tubes 9 (10) of the blood circuit to a pouch of sterile solution, connects the other small access tube 10 (9) to an empty collecting pouch, and makes the sterile solution circulate through the blood compartment, if appropriate by means of the blood pump of the dialysis machine. The sterile solution dissolves the substance and carries it into contact with the surface to be treated, where it is bonded, for example by ionic or covalent bonding.

In the exemplary of embodiment just described, it is because the two small tubes 9, 10 for access to the blood compartment are symmetrical so as not to have to impose on the user a direction of circulation of the saline solution when the haemodialyser is being started up, that a quantity of appropriate substance (drops 11, 12) has been deposited in each of the end fittings. The substance which is deposited in the downstream end fitting during the start-up is therefore not employed for the treatment of the surface whose biocompatibility is to be improved. Naturally, by suitably marking the end fitting to which the pouch of saline solution is to be connected for starting up, it is possible to deposit the drop of the treatment substance in only one end fitting 7, 8.

According to an alternative form of the invention, instead of manufacturing a blood treatment apparatus according to the process described above, where a drop of appropriate substance is deposited in at least one of the small tubes 9, 10 for access to the blood compartment, a coupling is manufactured comprising a female portion matching these small tubes 9, 10, and a male portion matching the female connection member fitted to the end of the lines employed for connecting a patient to a blood treatment apparatus. This coupling is obtained by moulding or extruding a plastic which is suitable for contact with blood. A drop of the substance intended to improve the biocompatability of a blood treatment apparatus is deposited inside this coupling. The coupling is next placed in a packaging capable of forming a sterile barrier and then the whole is sterilized by γ irradiation. The coupling is fitted to a conventional blood treatment apparatus before the preliminary stage, described above, of starting-up the apparatus.

In one embodiment of the invention the portion of the haemodialyser whose biocompatibility is to be improved is a semipermeable membrane whose surface has negative charges. The aim of the improvement is to prevent the activation of the contact phase or to neutralize it. In accordance with the invention an appropriate substance exhibits the following characteristics:

1—it must be cationic, so as to bond to the membrane by ionic bonding and to mask negative charges on the surface of the membrane;

2—it must be soluble in water so as to be dissolvable in the aqueous solution employed for starting-up the apparatus;

3—it must not be toxic;

4—it must be macromolecular and its size must be chosen in such a way that a macromolecule does not enter the pores of the membrane (for example, in the case of the AN69 membrane, this size must be at least 10 k dalton). In the course of utilization, a macromolecule attached to the membrane will be difficult to displace from it with a blood protein. Also, a macromolecule which is prohibited by its size from entering biological cells is a priori less toxic than a molecule whose dimensions allow it to enter a cell;

5—it must, where appropriate, withstand an energetic sterilization, of the γ irradiation type, even if it is partially affected thereby. In other words, at least a proportion of the molecules must remain intact and be capable of bonding to the membrane in the desired manner. Furthermore, the irradiated substance must not become toxic;

6—once bonded to the membrane, it must not significantly alter the characteristics of the membrane (haemocompatibility, diffusive and convective transfer capacity, protein adsorption capacity).

To give an example, it has been discovered, in accordance with the invention, that PEI with a molecular mass of between 10 and 2000 k dalton, which is in the form of a water-soluble gel, is a wholly appropriate substance for the modification of the membrane known under the trade name AN69, the surface of which has negative charges. In particular, in-vitro tests have shown that the potential toxicity threshold of irradiated PEI corresponds to the injection of a quantity of PEI needed to raise the PEI concentration of an internal liquid (plasma) to 0.4 mg/ml (by way of comparison, if the quantity of PEI sufficient to treat a conventional dialyser, that is 10 mg, were injected into the blood of an adult, the PEI concentration in the plasma would be of the order of 0.002 mg/ml).

Another appropriate substance for the modification of the membrane known under the trade name AN69 is diethylaminoethyl dextran (DEAE dextran) with a mean molecular mass of 500 k dalton. Unlike PEI, this substance is not available in the form of a water-soluble gel, but of a powder. Thus, it is necessary to incorporate it into a gel of a neutral matrix material in order to be capable of employing it in accordance with the invention. To give an example, a carboxymethylcellulose gel can be employed for this purpose.

The main stages of the manufacture of a hollow fibre made of AN69 are recalled briefly. A solution of polymer is prepared, containing 35% by weight of a copolymer of acrylonitrile and of sodium methallylsulphonate, 52% by weight of dimethylformamide (DMF) and 13% by weight of glycerol. The polymer solution is heated to 130° C. and is extruded through a die which has two concentric nozzles, nitrogen being injected into the inner nozzle to form the aperture of the hollow fibre. Upon contact with the ambient air (approximately 20–25° C.), the thermoreversible gel fibre leaving the die is the site of a thermal phase inversion. The fibre is next received in a water bath in which the solvent (DMF) in the fibre is replaced with water. The fibre is next immersed in hot water at 95° C., where it is drawn approximately fourfold. A stage of stabilization in hot water at 95° C. follows. Finally, the fibre is glycerinated with a water/glycerol mixture.

The manufacture of a planar membrane from AN69 comprises the following stages. A solution of polymer is prepared, containing 21% by weight of a copolymer of acrylonitrile and of sodium methallylsulphonate and 79% by weight of dimethylformamide (DMF). After filtration and degassing, this polymer solution is extruded by means of a slot-shaped die onto a rotary roll heated to 80° C. Some of the DMF is evaporated off. The film obtained is drawn approximately three-and-a-halffold in hot water at 95° C. A stage of stabilization in hot water at 95° C. follows. Finally the membrane is glycerinated in a water/glycerol mixture.

EXAMPLE 1

A dialyser including approximately 8500 hollow AN69 fibres was assembled. Each fibre had the following dimensions: inner diameter: 240 $\mu$m, wall thickness: 50 $\mu$m, length: 0.225 m. The area of the membrane intended to come into contact with the blood was approximately 1.44 $m^2$. A drop of 10 mg of PEI (BASF Lupasol WF, molecular mass: 25 k dalton) was deposited in each small tube for access to the blood compartment, after which the tubes for access to the two compartments of the dialyser were closed with special stoppers and the dialyser was sterilized with ethylene oxide. Two liters of sterile physiological saline (solution of sodium chloride at a concentration of 0.9 g/l) at ambient temperature (22° C.) were circulated at a flow rate of 200 ml/min through the blood compartment of this dialyser. The physiological saline dissolved the drop of PEI gel and the PEI molecules circulated through the dialyser were bonded, by ionic bonding, to the sodium methallylsulphonate groups present at the surface of the membrane.

To measure whether the dialyser thus manufactured and prepared for use had the level of biocompatibility set as objective of the invention, this dialyser was subjected to the following test: a biological liquid was prepared, capable of stimulating the production of kallikreins in contact with a membrane charged negatively at the surface. The biological liquid used for the test consisted of human plasma lean in platelets, diluted to 5% in physiological saline containing added citrate (it is noted that the conditions of the test employed are far from the conditions of use of an apparatus for extracorporeal blood circulation: the dilution ratio is very high, the liquid chosen is plasma and not blood, the plasma contains added citrate and is hence acidified, whereas in dialysis the anticoagulant employed is heparin. These test conditions are chosen deliberately because they stimulate and amplify the activation of the contact phase). One and a half liters of this liquid were circulated in a closed circuit through the blood compartment of the dialyser at a flow rate of 100 ml/min for six hours. The plasma kallikreins were assayed in samples of liquid taken intermittently by means of a conventional chromogenic test, starting with the S 2302 substrate from the Biogenic company. The result of the determinations shows unequivocally that the dialyser manufactured in accordance with the invention does not cause a rise in the content of kallikreins in a dilute plasma.

It is pointed out that, bearing in mind the sensitivity of the chromogenic test employed, it is considered that there is no significant rise in the content of kallikreins if the kallikrein concentration remains below approximately 10 units per liter.

It is emphasized that, besides its efficiency insofar as the improvement in the biocompatibility of the dialyser described above is concerned, this process of manufacture has a major advantage, even when sterilization with ethylene oxide would in principle make it possible to attach the PEI to the membrane before the sterilization stage. In fact, bearing in mind that the AN69 fibres are glycerinated, if they were to be treated with PEI before the sterilization of the dialyser, it would be necessary:

1—to deglycerinate the fibres by rinsing the dialyser with an aqueous solution;

2—to circulate a solution of PEI through the blood compartment;

3—to reglycerinate the fibres in order to expel water therefrom, since ethylene oxide has no effect on a wet product; and 4—to purge the fibres of the excess glycerol.

Apart from the fact that the fourth stage would be difficult or even impossible to carry out, it will be understood that adding four additional stages to an industrial manufacturing process would make its cost prohibitive. To summarize, the process according to the invention, according to which the deglycerinating of the fibres and their treatment with PEI are done simultaneously when the dialyser is being started up, makes it possible to industrialize the improvement in the biocompatibility of a dialyser whose membrane is made of AN69.

EXAMPLE 2

A dialyser with a planar AN69 membrane was assembled. The membrane had a thickness of approximately 20 $\mu$m. The area of the membrane intended to come into contact with the blood was approximately 1.50 $m^2$. A drop of 10 mg of PEI (Lupasol WF, 25 k dalton) was deposited in each small tube for access to the blood compartment, after which the small tubes for access to the two compartments of the dialyser were closed off and the dialyser was sterilized by γ irradiation (36 kGy). Two liters of sterile physiological saline at ambient temperature (approximately 22° C.) were circulated through the blood compartment of this dialyser. The physiological saline dissolved the drop of PEI gel and the PEI molecules circulated through the dialyser were bonded to the sodium methallylsulphonate groups present at the surface of the membrane.

The dialyser was then subjected to the in-vitro test described in Example 1, intended to measure whether the AN69 membrane coated with a monolayer of PEI activates the contact phase. As in the case of the dialyser with hollow fibres, the test result was negative.

EXAMPLE 3

Figure 2:
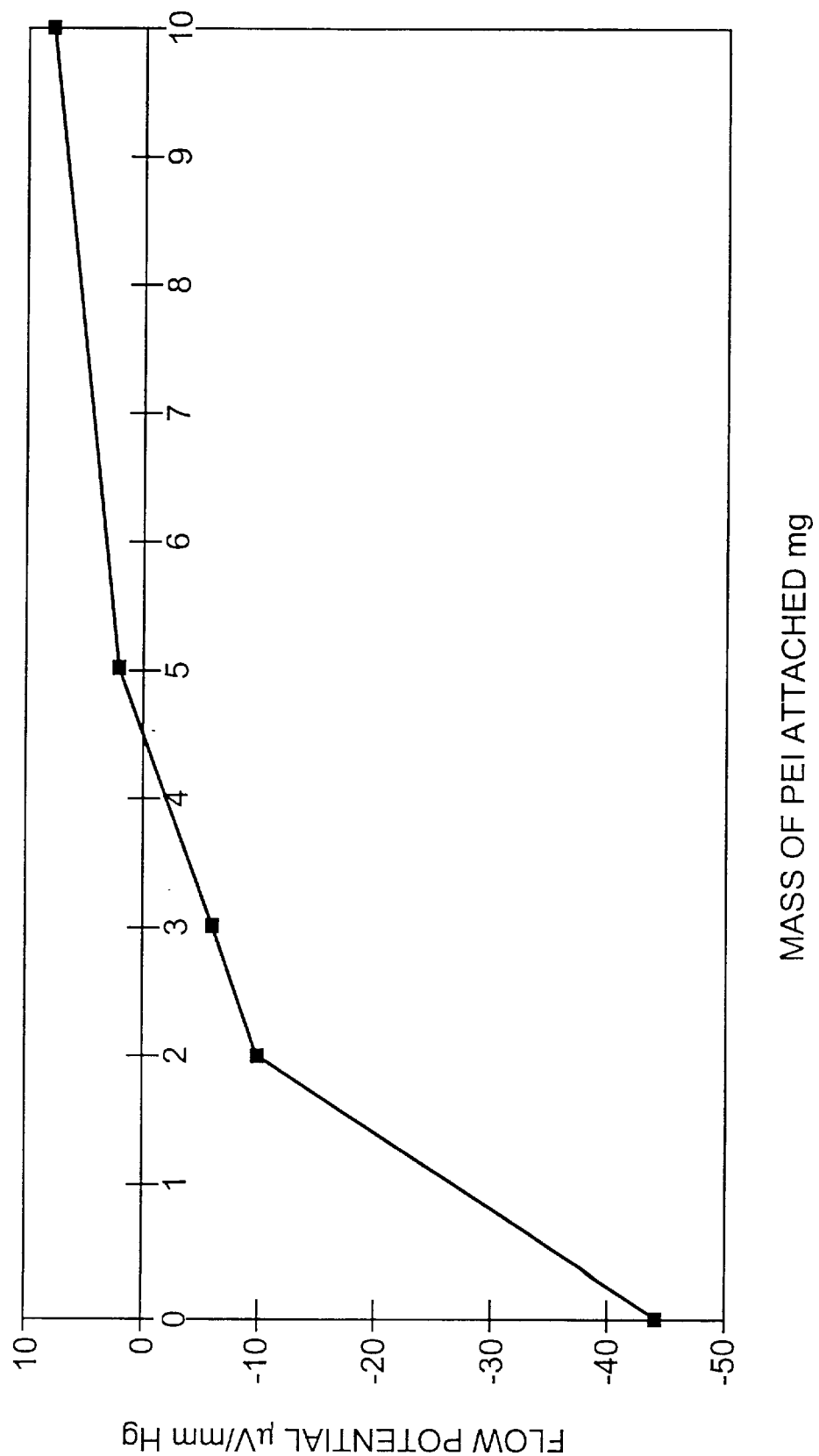
FIG. 2 shows the effect of the quantity of PEI employed for treating the AN69 membrane on the electrical surface potential of this membrane.
Figure 3:
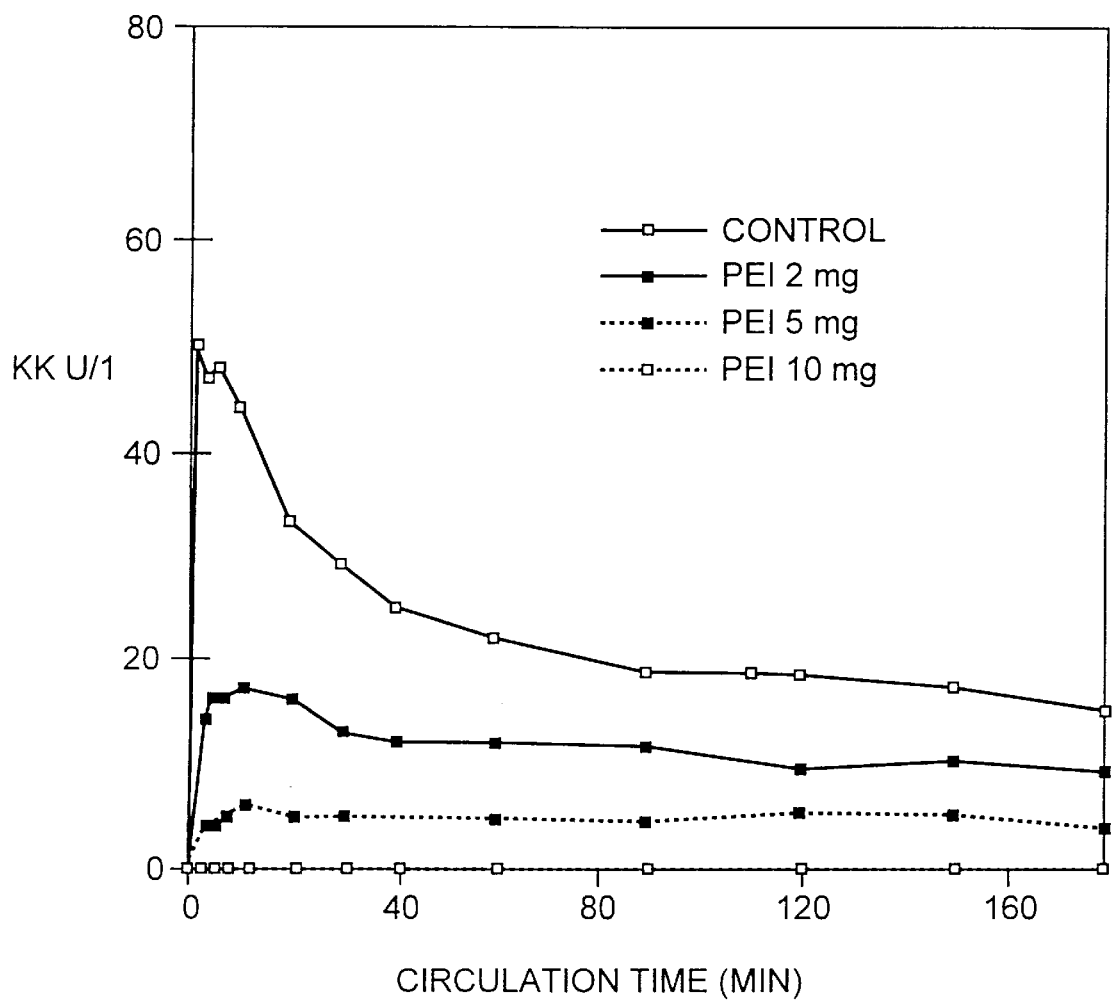
FIG. 3 shows the effect of the quantity of PEI (molecular mass: 25 k dalton) employed for treating the AN69 membrane on the activation of the contact phase.

The graph in FIG. 2 shows the result of in-vitro tests performed on a dialyser with a planar membrane of the type in Example 2, intended to determine the effect of the quantity of PEI (Lupasol WF, 25 k dalton) used per dialyser on the electrical surface charge of a membrane made of AN69. The electrical surface charge is evaluated by measuring the flow potential, as defined below: the starting point is that a solution of electrolyte circulating through the compartment of a dialyser generates a potential difference DE proportional to the pressure drop DP created by the electrolyte solution between the entry and the exit of the dialyser. After the dialyser has been rinsed and when its membrane has therefore been coated with PEI, a solution of sodium chloride ($10^{-2}$M) was circulated through the blood compartment and DE and DP were measured at the access points to the blood compartment, by means of Ag/AgCl electrodes and pressure sensors. The DE/DP ratio is called the flow potential of the electrolyte in the dialyser and this ratio is characteristic of the surface charge of the membrane.

In this diagram it can be seen that approximately 5 mg of PEI are sufficient to make the surface of the membrane electrically neutral.

EXAMPLE 4

Figure 4:
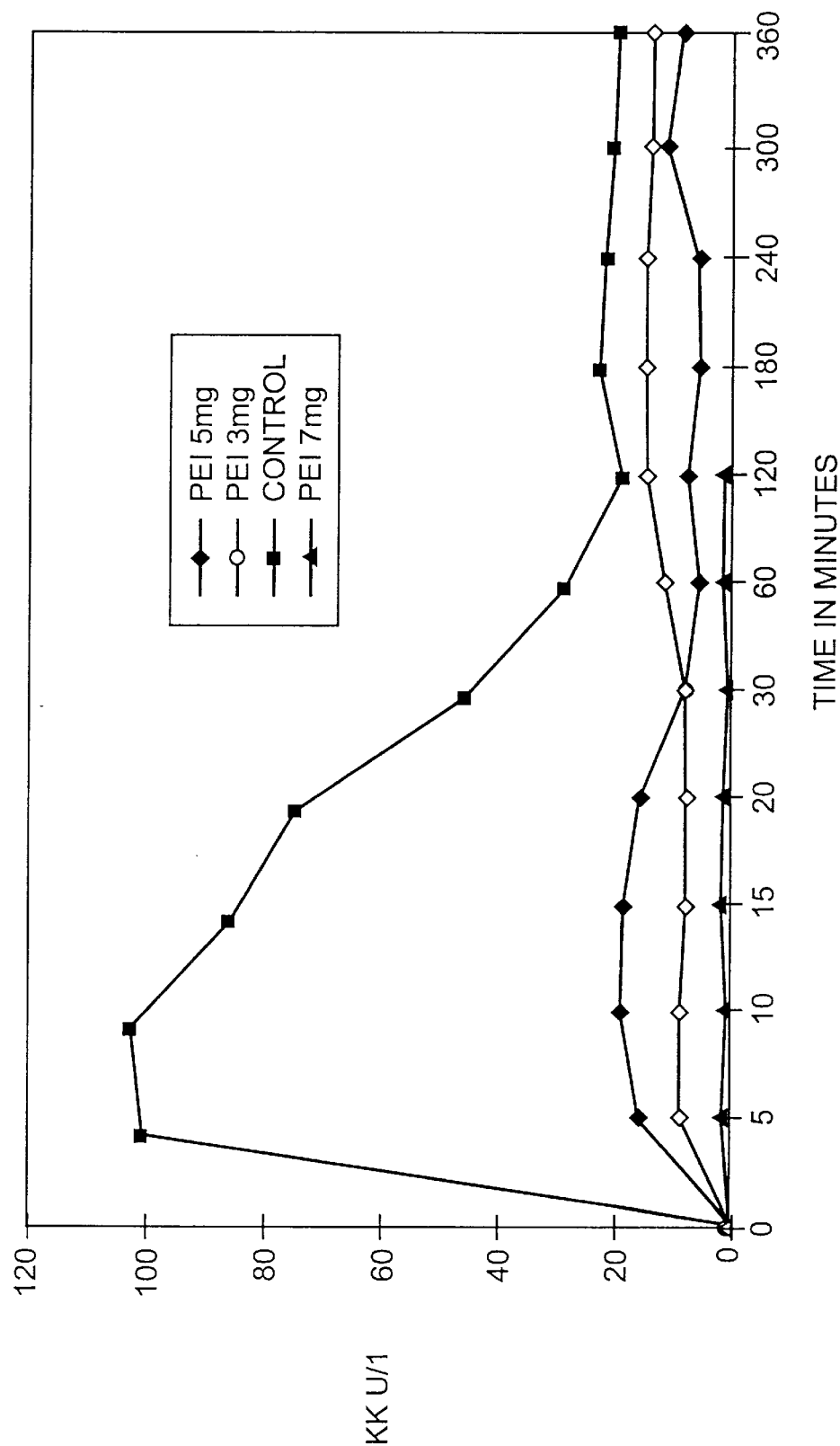
FIG. 4 shows the effect of the quantity of PEI (molecular mass: 750 k dalton) employed for treating the AN69 membrane on the activation of the contact phase.

The graph in FIG. 4 shows the result of in-vitro tests performed on a dialyser with a planar membrane of the type in Example 2, intended to determine the effect of the quantity of PEI (Lupasol WF, 25 k dalton) used per dialyser on the activation of the contact phase. The activation of the contact phase is evaluated by means of the generation of kallikreins according to the test described in Example 1. In this diagram it is seen that 10 mg of PEI (molecular mass 25 k dalton) are sufficient to completely suppress the activation of the contact phase.

EXAMPLE 5

The graph in FIG. 4 shows the result of in-vitro tests performed on a dialyser with a planar membrane of the type in Example 2, intended to determine the effect of the quantity of PEI (Lupasol P, 750 k dalton) used per dialyser on the activation of the contact phase. The activation of the contact phase is evaluated by means of the generation of kallikreins according to the test described in Example 1. In this diagram it is seen that 7 mg of PEI (molecular mass 750 k dalton) are sufficient to completely suppress the activation of the contact phase.

EXAMPLE 6

Figure 5:
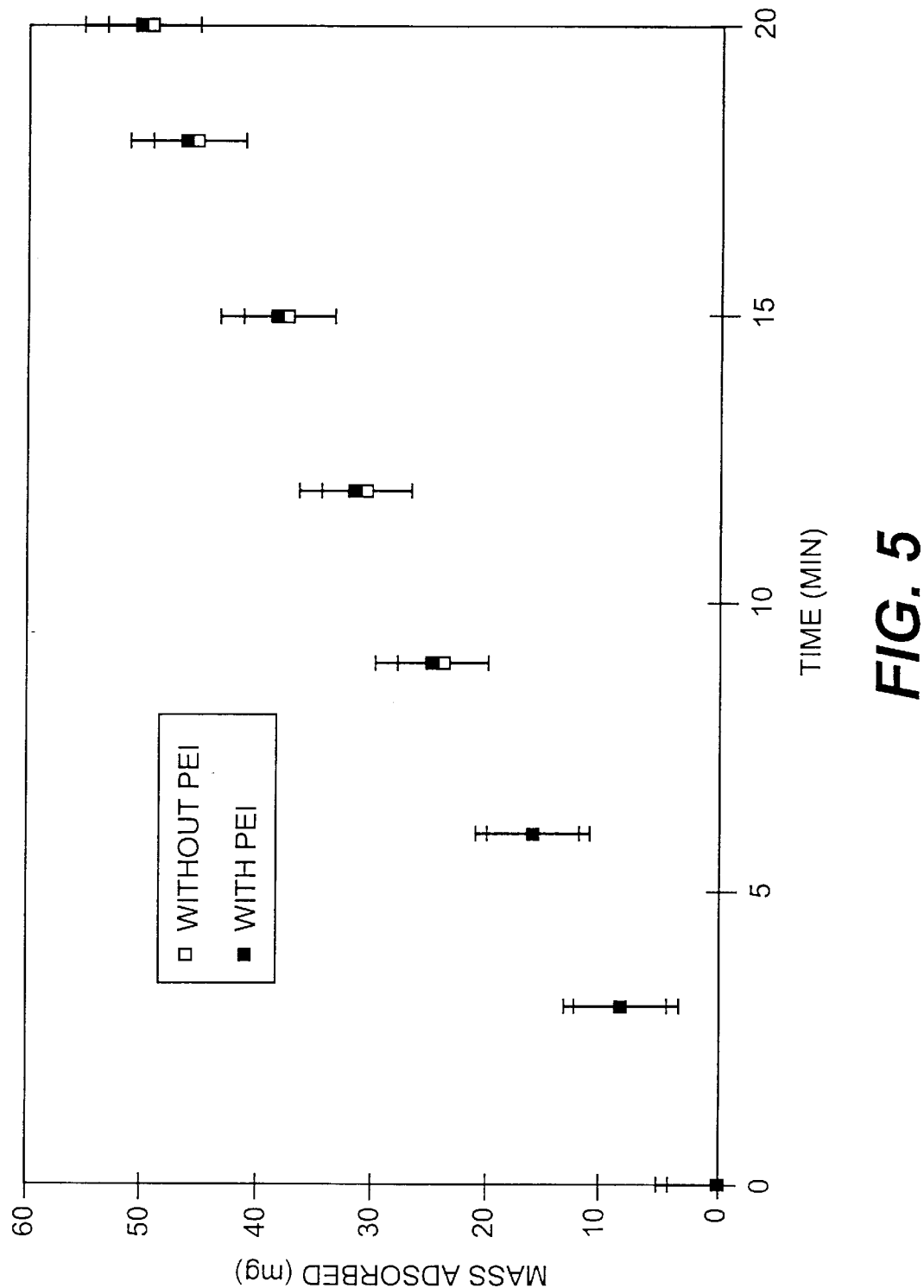
FIG. 5 shows the adsorption kinetics of Cytochrome C on a conventional AN69 membrane and on an AN69 membrane to which PEI has been bonded.

By employing cytochrome C as test molecule it was verified in vitro that the protein adsorption capacity within the bulk of the membrane remains unchanged after treatment of the membrane with PEI (Lupasol WF, 25 k dalton) with 10 mg per dialyser with a planar AN69 membrane which has an area of approximately 1.25 $m^2$. To perform this verification, the following test was carried out on two dialysers with a planar AN69 membrane (area of approximately 1.25 $m^2$), one of which had been treated with PEI and the other had not: six liters of a solution of cytochrome C at a concentration of 20 mg/l in a pH 7.4 phosphate buffer medium were circulated, in open circuit, at a flow rate of 300 ml/min, through the blood compartment of each dialyser. The concentration of cytochrome C in the solution leaving the dialyser was measured at regular time intervals and the cumulative quantity of cytochrome C adsorbed was calculated. FIG. 5 shows that the result of the measurements was the same for both dialysers.

EXAMPLE 7

It was also verified in vitro that the bonding of PEI to the membrane was completely irreversible and that PEI was not released back into a liquid circulated through the blood compartment of the dialyser. To perform this verification, two independent tests were performed:

1 st test: the flow potential of a solution of sodium chloride was measured (according to the method in Example 3) in the blood compartment of a dialyser of the type described in Example 2. Physiological saline was next circulated in open circuit at 37° C. at a flow rate of 300 ml/min for 5 hours, through the blood compartment of the dialyser. The flow potential of a sodium chloride solution was then measured again and the results of the two measurements were compared. Since they were identical, it was concluded that the bonding between the AN69 membrane and the PEI is durable.

2nd test: PEI (Lupasol P, 750 k dalton) was labelled with a molecule containing a radioactive isotope ([2,3-$^3$H]N-succimidyl propionate) by proceeding as follows: PEI was reacted with [2,3-$^3$H]N-succimidyl propionate to obtain $^3$H-PEI (labelled PEI) which was next precipitated with sulphosalicylic acid, to separate the labelled PEI from the excess [2,3-$^3$H]N-succimidyl propionate; the precipitate was then subjected to successive washings with water to remove the excess of [2,3-$^3$H]N-succimidyl propionate and to obtain labelled PEI which had a specific activity of 1.52 mCi/g (which corresponds to a mean substitution ratio of 11.7 mmol of 3H propionate per μmol of PEI).

A dialyser including approximately 8500 hollow AN69 fibres was manufactured in accordance with the process described in the first paragraph of Example 1, the only difference being that it was one drop of 10 mg of labelled PEI that was deposited in each small tube for access to the blood compartment of the dialyser, instead of standard PEI (BASF Lupasol WF, molecular mass: 25 k dalton).

Through the blood compartment of this dialyser was circulated in closed circuit for four hours 0.51 of whole human blood containing heparin at a concentration of 3 IU/ml (standard heparin marketed by PAN Pharma). A sample of blood circulating through the dialyser was taken every half hour and its radioactivity was measured. No desorption of labelled PEI was detected in any sample (bearing in mind the means of measurement employed, it is considered that the detection limit was 0.4 μg/ml).

EXAMPLE 8

An experimental membrane M was manufactured in the form of a hollow fibre according to the following stages. A solution of polymer was prepared containing 28% by weight of a copolymer of acrylonitrile and vinyl acetate, 51% by weight of dimethylformamide (DMF) and 21% by weight of glycerol. The polymer solution was heated to 120° C. and was extruded through a die which had two concentric nozzles, nitrogen being injected into the inner nozzle to form the aperture of the hollow fibre. Upon contact with the ambient air (approximately 20–25° C.) the thermoreversible gel fibre leaving the die was the site of a thermal phase inversion. The fibre was next received in a water bath in which the solvent (DMF) in the fibre was replaced with water. The fibre was next immersed in hot water at 40° C., where it was drawn approximately twofold. The resulting fibre was next stabilized in hot water at 60° C. Finally the fibre was glycerinated in a water/glycerol mixture.

A dialyser including approximately 10,000 hollow M fibres was assembled. Each fibre had the following dimensions: inner diameter: 190 μm; wall thickness: 50 μm; length: 0.225 m. The area of the membrane intended to come into contact with the blood was approximately 1.34 m². A drop of 12 mg of PEI (Lupasol WF; molecular mass: 25 k dalton) was deposited in each small tube for access to the blood compartment. Two liters of sterile physiological saline (solution of sodium chloride at a concentration of 0.9 g/l) at ambient temperature (22° C.) were circulated at a flow rate of 200 ml/min through the blood compartment of this dialyser. The physiological saline dissolved the drop of PEI gel and the PEI molecules circulated through the dialyser were bonded, by ionic bonding, to the surface of the membrane.

Figure 6:
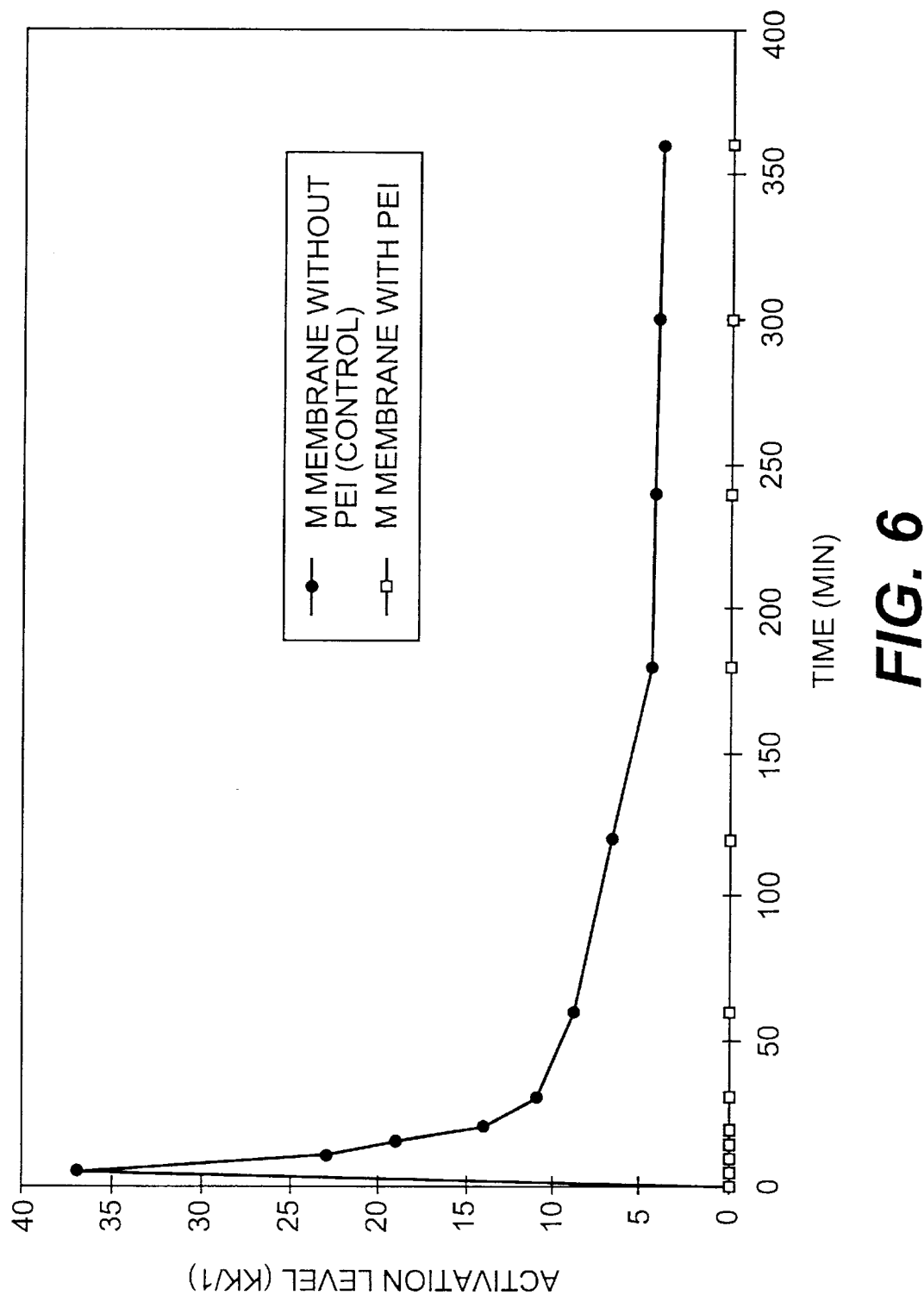
FIG. 6 shows the level of activation of the contact phase by an experimental membrane devoid of PEI and by the same membrane to which PEI has been bonded.

The dialyser was then subjected to the in-vitro test described in Example 1, intended to measure whether the M membrane coated with a PEI monolayer activates the contact phase. As in the case of the dialyser with hollow fibres, the test result was negative. FIG. 6 shows the activation level caused by this dialyser and the activation level caused by a dialyser of the same manufacture but whose membrane has not been coated with PEI.

EXAMPLE 9

The effectiveness of the invention was verified on a dialyser with hollow fibres, equipped with a commercially available polyacrylonitrile-based membrane, namely a PAN 13 DX model dialyser (membrane working area: 1.3 m²) manufactured by Asahi. This dialyser was treated in accordance with the process described in the first paragraph of Example 1, the only difference being that it was one drop of 10 mg of PEI of molecular mass 750 k dalton (BASF Lupasol P) that was deposited in the small tube for entry to the blood compartment of the dialyser, instead of PEI of molecular mass 25 k dalton (BASF Lupasol WF).

Figure 7:
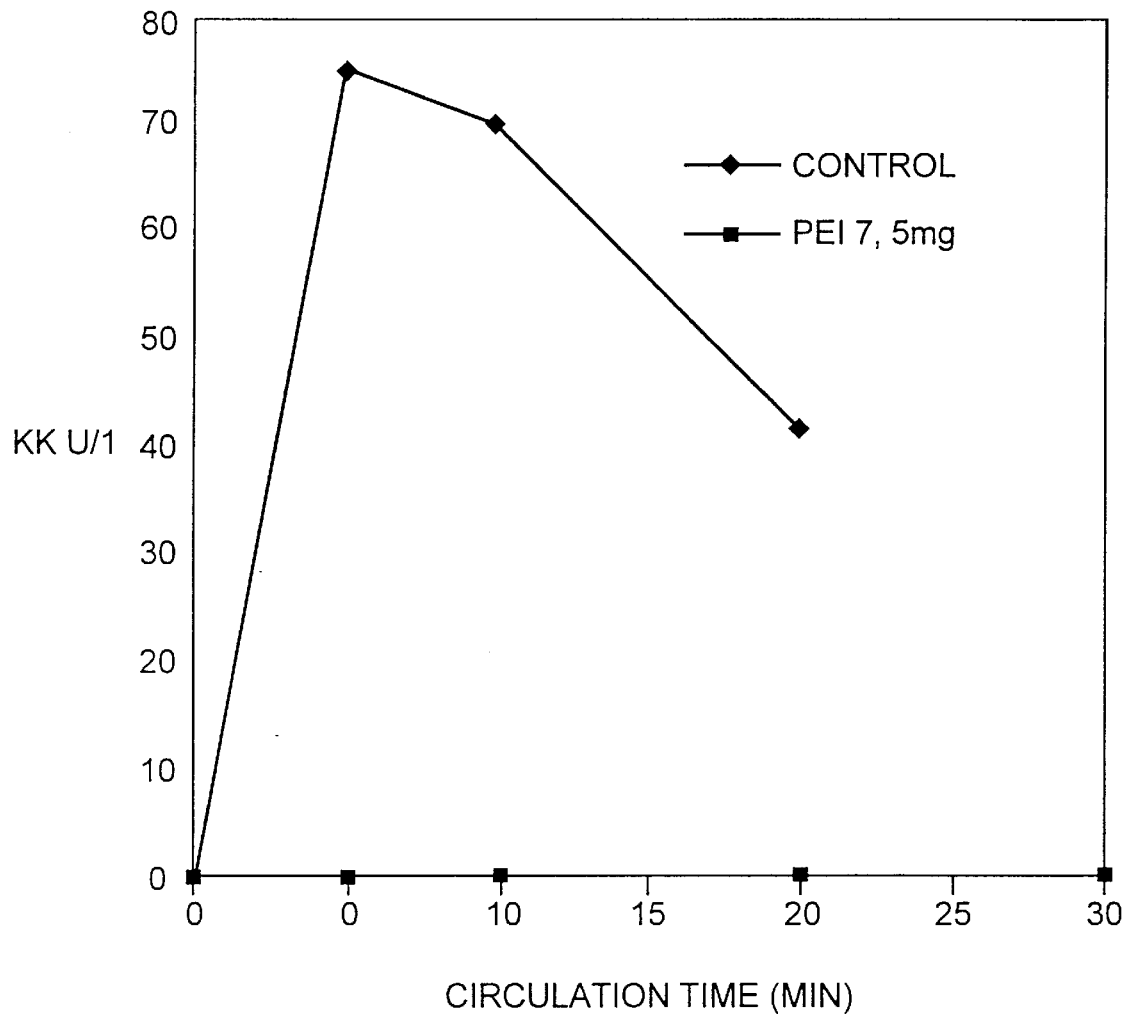
FIG. 7 shows the level of activation of the contact phase by a membrane based on polyacrylonitrile devoid of PEI and by the same membrane to which PEI has been bonded.

The PAN 13 DX model dialyser was then subjected to the in-vitro test described in Example 1, intended to measure whether the membrane coated with a PEI monolayer activates the contact phase. The test result was negative. FIG. 7 shows the activation level caused by this dialyser and the activation level caused by a dialyser of the same manufacture but whose membrane has not been coated with PEI.

EXAMPLE 10

The feasibility of the invention was verified by employing, as substance intended to modify a membrane, not a substance available in gel form (like PEI), but a substance available in powder form.

A water-soluble gel which was nontoxic and chemically neutral towards the AN69 membrane was prepared by dissolving carboxymethylcellulose (C5678 from Sigma) at ambient temperature (25° C.) in demineralized water in a proportion of 12.5 mass % of carboxymethylcellulose and 87.5 mass % of water. Into this neutral matrix was incorporated, as active substance, diethylaminoethyl dextran (D 1162 from Sigma) of mean molecular mass 500 k dalton, in a proportion of 500 mass % of DEAE dextran and 50 mass % of carboxymethylcellulose gel.

A dialyser including approximately 8500 hollow AN69 fibres was assembled. Each fibre had the following dimensions: inner diameter: 240 μm; wall thickness: 50 μm; length: 0.225 m. The area of the membrane intended to come into contact with the blood was approximately 1.44 m². A drop of 100 mg of the neutral gel/active substance mixture (that is 50 mg of DEAE dextran) was deposited in a small tube for access to the blood compartment. Two liters of sterile physiological saline (solution of sodium chloride at a concentration of 0.9 g/l) at ambient temperature (25° C.) were circulated at a flow rate of 200 ml/min through the blood compartment of this dialyser starting from the access where the drop of neutral gel/active substance mixture was deposited. The physiological saline dissolved the drop of gel and the DEAE dextran molecules circulated through the dialyser were bonded, by ionic bonding, to the sodium methallylsulphonate groups present at the surface of the membrane.

Figure 8:
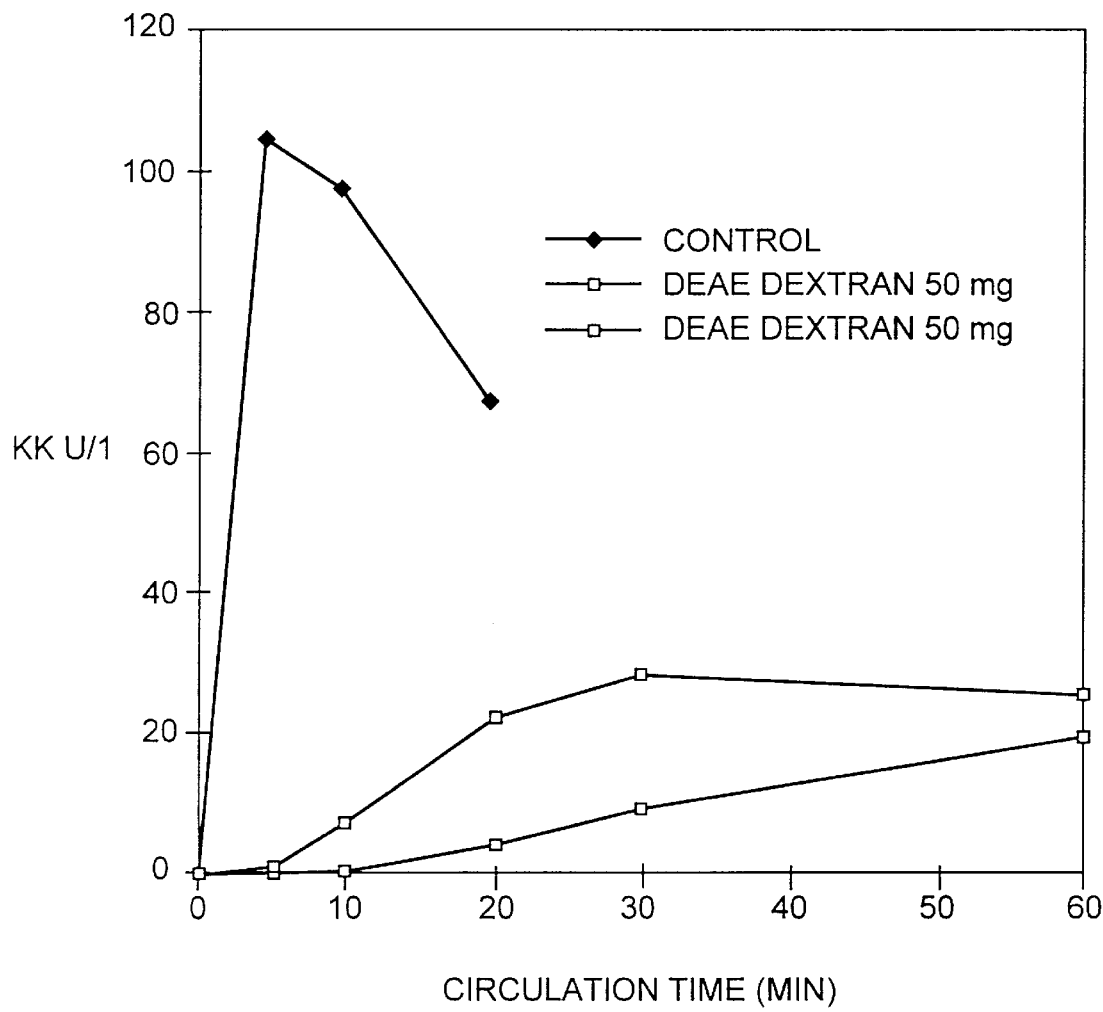
FIG. 8 shows the degree of activation of the contact phase by a membrane made of AN69 devoid of DEAE dextran and by the same membrane to which DEAE dextran has been bonded.
Figure 9A:
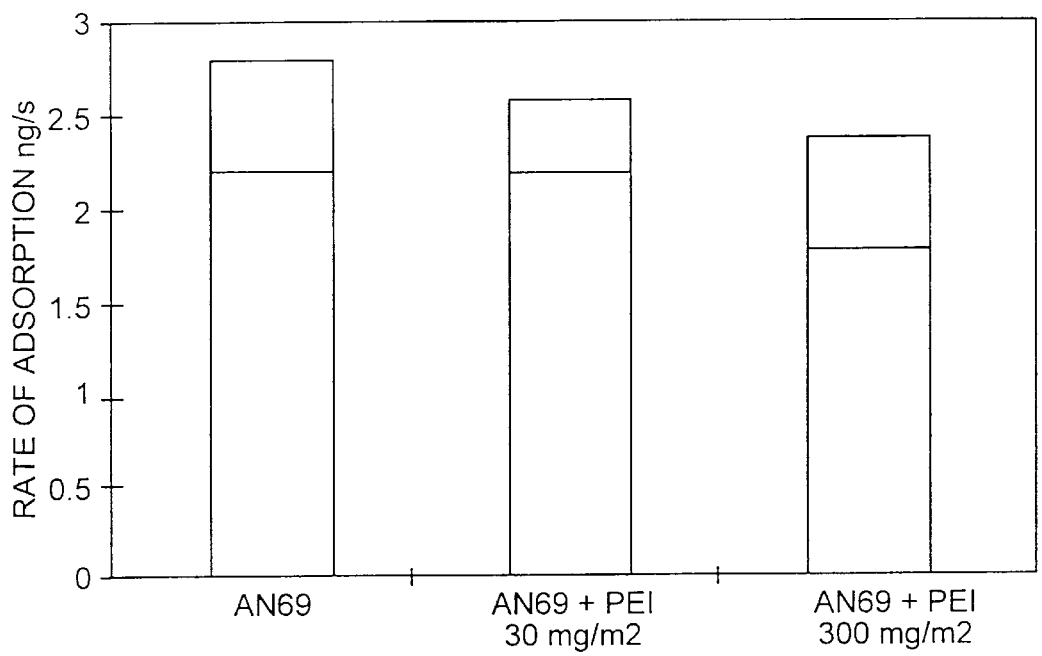
FIGS. 9a and 9b illustrate the haemocompatibility of a dialysis membrane according to the invention.
Figure 9B:
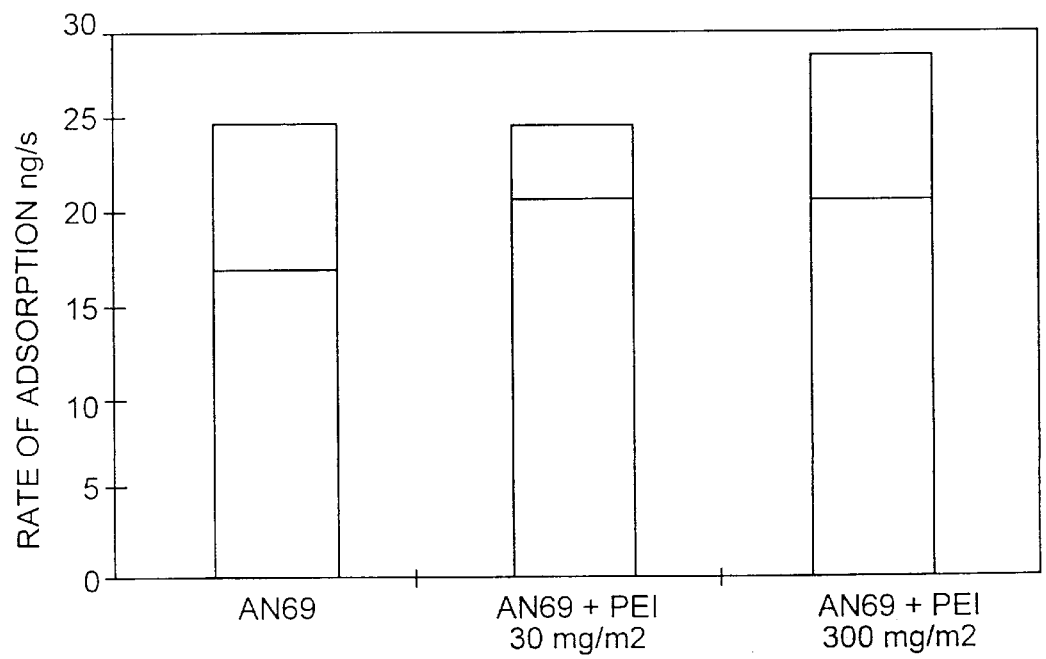

To measure whether and—where appropriate—to what extent, the dialyser thus manufactured activated the contact phase, it was subjected to the test described in Example 1, the only variant being that the human plasma diluted to 5% in physiological saline was circulated through the blood compartment of the dialyser for one hour instead of six, which was sufficient, bearing in mind the objective of the verification performed. The result of the determinations shows unequivocally that this dialyser produces only a weak activation of the contact phase (FIG. 8). It should be noted that, bearing in mind the objective aimed at, no attempt was made in this example to optimize the parameters which make it possible to obtain the total neutralization of the contact phase, in particular the quantity of active substance and the viscosity of the matrix gel.

To finish with, the dialyser treated with PEI was subjected to a whole series of conventional measurements intended to determine its characteristics: toxicity, haemocompatibility, diffusive and convective transfer capacity and the like. The characteristics of the treated dialyser were at least as good as those of an untreated dialyser of the same type.

Toxicity test

Two batches of dialysers which had a membrane made up of hollow AN69 fibres were assembled, each fibre having the following dimensions: inner diameter: 210 μm, wall thickness: 42 μm. The dialysers of the first batch included approximately 9024 fibres (length: 0.24 m) and the dialysers of the second batch included approximately 11520 fibres (length: 0.30 m), the area of the membrane intended to come into contact with the blood being approximately 1.43 m² in the first case and approximately 2.26 m² in the second case. Each dialyser was next subjected to a treatment including the stages of:

1) deglycerinating the fibres by rinsing the dialyser with water;
2) circulating for 6 min through the blood compartment, in open circuit, at a flow rate of 200 ml/min, an aqueous solution of PEI (Lupasol WF, molecular mass: 25 k dalton) at a concentration of 1 g/l. At the end of this stage approximately 340 mg of PEI were attached to the membrane of a dialyser of the first batch (approximately 9024 fibres) and approximately 500 mg of PEI were attached to the membrane of a dialyser of the second batch (approximately 11520 fibres);

3) sterilizing the dialyser by γ irradiation (36 kGy).

It is noted that the quantity of PEI attached to the membrane of these dialysers was much greater than the quantity attached to the membrane of the dialysers of Examples 1, 2 and 8 and that the sterilization was performed when the PEI was already bonded to the membrane.

These dialysers satisfied the tests for biological evaluation of medical devices, defined in international standard ISO 10993-1.

Evaluation of haemocompatibility

The haemocompatibility of a dialysis membrane, and in particular its nonthrombogenic nature is linked with its protein adsorption properties at the surface of the membrane in contact with the blood.

The adsorption kinetics of fibrinogen labelled with iodine 125 were measured in vitro on small-scale dialysers which had a membrane made up of AN69 fibres, in hydrodynamic conditions comparable with those of a dialysis session.

The small-scale model dialysers employed for the test included 170 AN69 fibres (inner diameter: 210 $\mu$m, wall thickness: 42 $\mu$m, length: 0.18 m) whose surface intended to come into contact with the blood had been treated with PEI in accordance with the invention (approximately 30 mg/m$^2$, respectively 300 mg/m$^2$, in the case of the minidialysers in the blood compartment of which the drop of PEI deposited was of 0.7 mg, respectively of 7 mg).

Heparin-containing human blood containing radiolabelled fibrinogen in a concentration of 2.5 $\mu$g/ml was prepared and this liquid was circulated, in open circuit, at a flow rate of 2.5 ml/min in a control minidialyser (AN69 without PEI) and in a minidialyser according to the invention. The rate of absorption of the fibrinogen, determined by means of the measurement of the radioactivity of the minidialyser, is shown in FIG. 8b. It was found that this rate was substantially the same for a control minidialyser and for the minidialysers to the membrane of which PEI has been attached.

The same test was performed with a solution of radioactively labelled fibrinogen in a pH 7.4 buffer liquid (concentration of 2.5 $\mu$g/ml). As can be seen in FIG. 8a, here, too, the rate of adsorption is substantially the same for a control minidialyser and for a minidialyser to the membrane of which PEI has been attached.

Convective transfer capacity

The ultrafiltration gradient and the maximum ultrafiltration flow rate were measured for two control dialysers (No. 1 and 2) which had a planar AN69 membrane with an area of 1.53 m$^2$ and two dialysers (No. 3 and 4) which had a planar AN69 membrane with an area of 1.53 m$^2$, prepared according to the process described in Example 2 with 12 mg of PEI (BASF Lupasol WF, molecular mass: 25 k dalton).

The measurement of the ultrafiltration gradient and the measurement of the maximum ultrafiltration flow rate were performed in the following manner: heparin-containing and standardized ox blood (protein content of 60 g/l and hematocrit of 32%) was circulated through the blood compartment of the dialyser at the steady flow rate of 300 ml/min. An ultrafiltration of the blood through the membrane was produced by means of a pump connected to the second compartment of the dialyser. By gradually increasing the ultrafiltration flow rate the transmembrane pressure (TMP) is increased and is measured continuously with the aid of two pressure sensors connected respectively to the two compartments of the dialyser, and the ultrafiltration gradient in ml/h mm Hg is deduced from this. Starting from a threshold value, the ultrafiltration flow rate remains stable even if the TMP continues to increase. The maximum ultrafiltration flow rate in ml/min is then measured.

The table below shows the result of these measurements, which shows that the conventional dialysers and the dialysers according to the invention have equivalent convective transfer capacities.

| Dialyser No. | Ultrafiltration gradient (ml/h mm Hg | Maximum ultra-filtration flow rate (ml/min) |
| --- | --- | --- |
| 1 | 39 | 100 |
| 2 | 43 | 104 |
| 3 | 43 | 107 |
| 4 | 45 | 104 |

The present invention is not limited to the example just described and can have alternative forms.

We claim:

1. Apparatus for the treatment of blood or plasma by extracorporeal circulation, comprising:

a compartment for the circulation of blood, provided with two accesses, the compartment having at least one inner surface intended to be coated, after sterilization, with at least one molecular layer of a substance soluble in an aqueous solution and capable of increasing biocompatibility of the at least one inner surface; and a determined quantity of the substance deposited inside the blood compartment, at one of the accesses, in a form such that the substance is capable of undergoing, substantially without deterioration, an irradiation capable of sterilizing the apparatus, the determined quantity of the substance being determined such that the circulation of a determined volume of aqueous solution through the blood compartment, starting from the access where the determined quantity of the substance has been deposited, should result in the formation, by durable bonding, of at least one molecular layer of the substance on the at least one inner surface of the blood compartment.

2. Apparatus according to claim 1, wherein the two accesses are symmetrical, and wherein the determined quantity of the substance is deposited at each access so that, whatever the direction of the subsequent circulation of the aqueous solution through the blood compartment, the molecular layer of the substance is formed on the inner surface to be treated.

3. Apparatus according to claim 1, wherein the determined quantity of the substance is in the form of a drop of a gel of the substance.

4. Apparatus according to claim 1, wherein the determined quantity of the substance is in the form of a drop of a matrix material in which the substance is incorporated.

5. Apparatus according to claim 1, wherein the inner surface to be treated has negative charges, and wherein the substance is cationic, with the result that a molecular layer of the substance masks the negative charges of the surface.

6. Apparatus according to claim 1, wherein the apparatus include a haemodialyser/haemofilter including two compartments separated by a semipermeable membrane, a first compartment being the compartment for the circulation of bloods and a second compartment being intended for the circulation of spent liquid, wherein the inner surface to be treated is the surface of the semipermeable membrane situated within the first compartment.

7. Apparatus according to claim 6, wherein the membrane is manufactured from an acrylonitrile copolymer, and wherein the substance is polyethyleneimine.

8. Apparatus according to claim 7, wherein the polyethyleneimine has a molecular mass of between approximately 10 and approximately 2000 k dalton.

9. Apparatus according to claim 8, wherein the polyethyleneimine has a molecular mass of 25 k dalton.

10. Apparatus according to claim 8, wherein the polyethyleneimine has a molecular mass of 750 k dalton.

11. Apparatus according to claim 8, wherein the quantity of polyethyleneimine of molecular mass of 25 k dalton deposited at one or each of the accesses is between approximately 5 mg and approximately 10 mg per $m^2$ of active membrane.

12. Apparatus according to claim 6, wherein the membrane is a planar membrane.

13. Apparatus according to claim 6, wherein the membrane consists of a bundle of hollow fibres.

14. Process of manufacture of an apparatus for the treatment of blood or plasma by extracorporeal circulation, the apparatus having a compartment for the circulation of blood provided with two accesses, the process comprising:

before a step of sterilization of the apparatus, the step of depositing in the blood compartment, at at least one of the accesses, a determined quantity of a substance in a form such that the substance is capable of undergoing, substantially without deterioration, an irradiation capable of sterilizing the apparatus, the substance being capable of dissolving in an aqueous solution and of durably bonding to an inner surface of the blood compartment in order to increase bicompatibility of said inner surface, the determined quantity of the substance being determined such that the circulation of a determined volume of aqueous solution through the blood compartment, starting from the access where the determined quantity of the substance has been deposited, should result in the formation, by durable bonding, of at least one molecular layer of the substance on said inner surface of the blood compartment.

15. Process for improving the biocompatibility of an apparatus for the treatment of blood or plasma by extracorporeal circulation, the apparatus having a compartment for the circulation of blood provided with two accesses, the process comprising the steps of:

depositing in the blood compartment, at at least one of the accesses, a determined quantity of a substance in a form such that the substance is capable of undergoing, substantially without deterioration, an irradiation capable of sterilizing the apparatus, the substance being capable of dissolving in an aqueous solution and of durably bonding to an inner surface of the blood compartment in order to increase biocompatibility of the inner surface of the blood compartment, the determined quantity of the substance being determined such that the circulation of a determined volume of aqueous solution through the blood compartment, starting from the access where the determined quantity of the substance has been deposited, should result in the formation, by durable bonding, of at least one molecular layer of the substance on the inner surface of the blood compartment;

sterilizing the apparatus; and before the utilization of the apparatus, circulating the determined volume of aqueous solution through the blood compartment, starting from the access where the determined quantity of the substance has been deposited, so as to carry the substance into contact with the inner surface of the blood compartment and to cause the formation of at least one durable molecular layer of the substance on the inner surface of the blood compartment.

16. Process according to either of claim 14 or claim 15, wherein the two accesses are symmetrical, and wherein the determined quantity of the substance is deposited at each access so that, whatever the direction of the subsequent circulation of the aqueous solution through the blood compartment, the molecular layer of the substance is formed on the inner surface to be treated.

17. Process according to either claim 14 or claim 15, wherein the determined quantity of the substance is deposited in the form of a drop of a gel of the substance.

18. Process of manufacture according to either claim 14 or claim 15, wherein the determined quantity of the substance is deposited in the form of a drop of a matrix material in which the substance is incorporated, the matrix material being soluble in an aqueous solution.

19. Process according to claim 15, wherein the apparatus is sterilized by means of ethylene oxide.

20. Process according to claim 15, wherein the apparatus is sterilized by $\gamma$ irradiation.

* * * * *